United States Patent
Mollenkopf

(10) Patent No.: US 6,794,540 B2
(45) Date of Patent: Sep. 21, 2004

(54) PROCESS FOR THE PREPARATION OF SORBIC ACID

(75) Inventor: Christoph Mollenkopf, Frankfurt (DE)

(73) Assignee: Nutrinova Nutrition Specialties & Food Ingredients GmbH, Wiesbaden (DE)

(*) Notice: Subject to any disclaimer, the term of this patent is extended or adjusted under 35 U.S.C. 154(b) by 0 days.

(21) Appl. No.: 10/336,294

(22) Filed: Jan. 3, 2003

(65) Prior Publication Data

US 2003/0130541 A1 Jul. 10, 2003

(30) Foreign Application Priority Data

Jan. 4, 2002 (DE) .......................... 102 00 200

(51) Int. Cl.$^7$ .................................. C07C 57/10
(52) U.S. Cl. ........................... 562/601; 562/598
(58) Field of Search .................. 562/598, 600, 562/601, 512

(56) References Cited

U.S. PATENT DOCUMENTS

| | | | |
|---|---|---|---|
| 3,461,158 A | 8/1969 | Hörnig et al. ........... 260/501.1 |
| 3,499,029 A | 3/1970 | Fernholz et al. ............ 260/526 |
| 3,696,147 A | 10/1972 | Kunstle et al. ............. 260/526 |
| 4,740,617 A | 4/1988 | Hallcher ..................... 562/599 |
| 2003/0060658 A1 * | 3/2003 | Decker et al. .............. 562/525 |
| 2003/0065218 A1 * | 4/2003 | Mollenkopf et al. ........ 562/601 |

FOREIGN PATENT DOCUMENTS

| | | |
|---|---|---|
| DE | 1 042 573 | 6/1956 |
| DE | 1 059 899 | 7/1956 |
| DE | 1 282 645 | 12/1964 |

* cited by examiner

Primary Examiner—Johann Richter
Assistant Examiner—Karl Puttlitz
(74) Attorney, Agent, or Firm—ProPat, L.L.C.

(57) ABSTRACT

A process for the preparation of sorbic acid by thermal cleavage of the polyester prepared from crotonaldehyde and ketene, in the presence of a solvent and of an amine as catalyst with simultaneous distillation out of the sorbic acid formed and of the solvent through a rectification column with reflux, wherein only the solvent rather than the distillate is used as reflux, leads to high yields of sorbic acid and to a reduced consumption of amine catalyst.

7 Claims, 1 Drawing Sheet

Flow diagram 1:
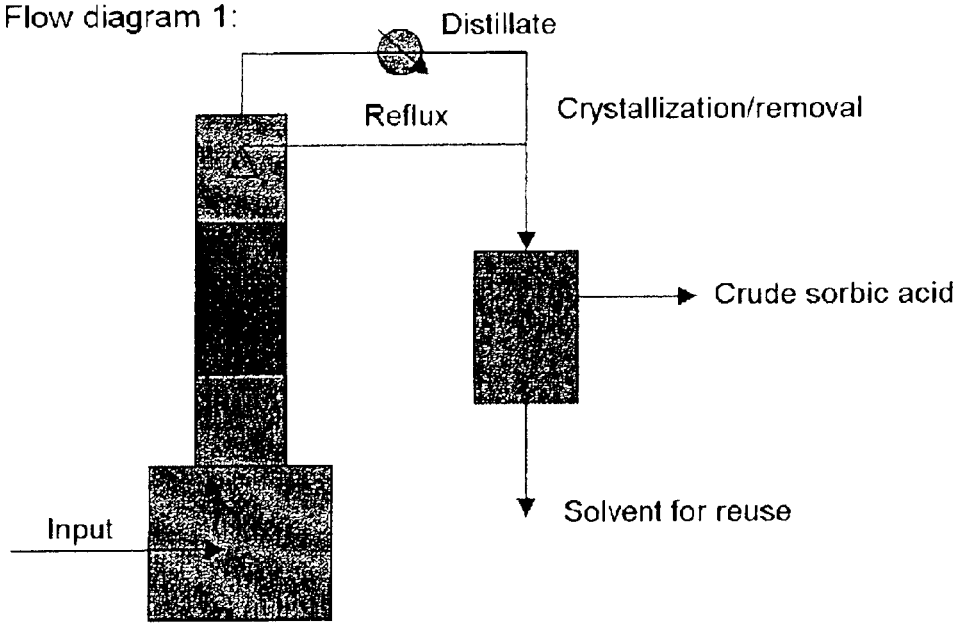
Flow diagram 2:
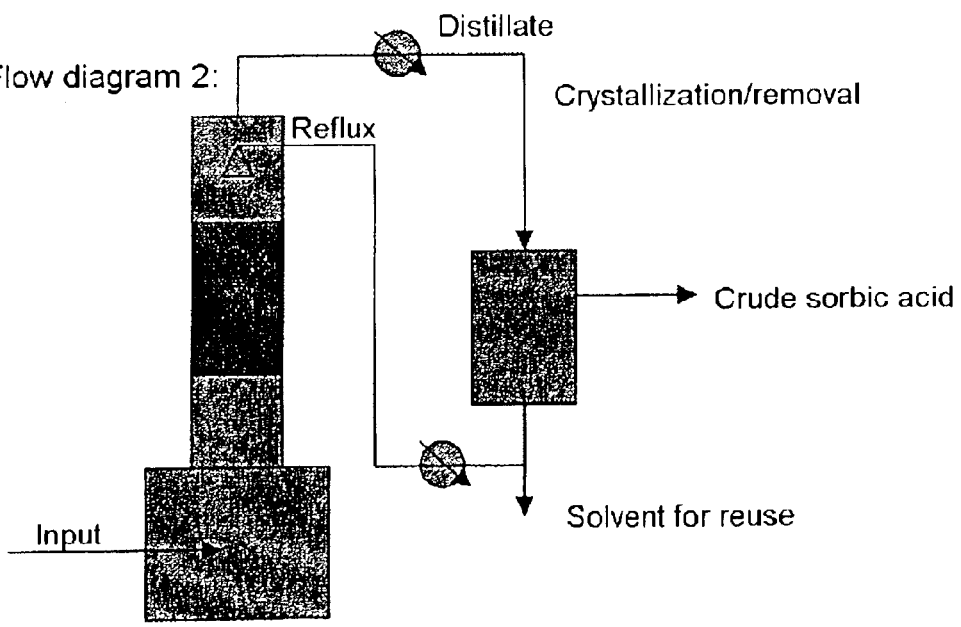

PROCESS FOR THE PREPARATION OF SORBIC ACID

BACKGROUND OF THE INVENTION

Various processes are known for the preparation of sorbic acid.

A particularly commercial process starts from the polymeric polyester reaction product prepared by reacting crotonaldehyde with ketene in an inert solvent in the presence of a fatty acid salt of a divalent and/or trivalent metal of group IIB to VIII of the periodic table as catalyst. The sorbic acid is obtained therefrom by alkaline hydrolysis and reaction with a strong acid (DE-AS 1 042 573).

However, sorbic acid can be obtained in various ways from this polyester.

DE-AS 1 059 899 describes the cleavage of the polyester to sorbic acid in the presence of an inert solvent which boils above 150° C. This solvent acts simultaneously as solvent for the polyester and as entrainer for the distillation of the sorbic acid formed therefrom. Alkali metal hydroxides or alkaline salts of organic acids are added as catalyst to the polyester or the mixture containing the latter.

An industrially important process for preparing sorbic acid consists of carrying out the cleavage of the polyester in the presence of an amine which boils above 150° C. as catalyst at temperatures of from 160 to 220° C. with simultaneous distillation out of the sorbic acid and of the solvent (DE-AS 1 282 645). The solvents used in this case are the solvents mentioned in DE-AS 1 059 899, in particular the aliphatic carboxylic acids having an appropriate boiling point mentioned therein.

When this process is carried out industrially, the polyester cleavage is carried out in a continuously operated distillation apparatus. The sorbic acid polyester dissolved in the solvent is metered into the distillation vessel where the amine-catalysed cleavage of the sorbic acid polyester to sorbic acid takes place. The sorbic acid which is formed is distilled out together with the solvent through a rectification column with reflux. The reflux is thus the distillate, i.e. a mixture of solvent and sorbic acid. The rectification is necessary in order to prevent the amine passing into the distillate and in order to achieve an appropriate purity of the sorbic acid. The sorbic acid is then crystallized out of the distillate and separated from the solvent. The solvent is recycled.

In the thermal cleavage of sorbic acid polyester there is formation in the distillation vessel not only of sorbic acid but also of polymers which must be continuously discharged. However, amine catalyst is also discharged thereby. On the one hand, this means a not inconsiderable loss of yield due to polymer formation and, on the other hand, amine catalyst must be continuously fed in to compensate for the losses due to the discharge.

The object therefore was to develop a process in which the polymer formation during the cleavage of sorbic acid polyester is reduced and thus both the yield of sorbic acid is increased and the consumption of amine is reduced.

BRIEF DESCRIPTION OF THE INVENTION

It has now been found, surprisingly, that polymer formation during the distillation can be markedly reduced with only the solvent, and not the distillate as in the prior art, is used as reflux. The result is a very pure sorbic acid with, at the same time, an increased yield and a reduction in the necessary input of amine as catalyst.

Flow diagram 1 shows diagrammatically the distillation process used in the prior art for the polyester cleavage, in which distillate taken off at the top of the column (mixture of sorbic acid and solvent) is fed as reflux into the rectification column.

Flow diagram 2 shows diagrammatically the distillation process according to the present invention, in which the solvent which has distilled out is, after removal of the sorbic acid, fed as reflux into the rectification column.

DETAILED DESCRIPTION OF THE INVENTION

The present invention thus relates to a process for the preparation of sorbic acid by thermal cleavage of the polyester prepared from crotonaldehyde and ketene, in the presence of a solvent and of an amine as catalyst with simultaneous distillation out of the sorbic acid and of the solvent through a rectification column with reflux, wherein the solvent is used as reflux.

It is possible and advantageous to carry out the process of the invention in such a way that all the vapours produced are cooled to crystallize the sorbic acid, the crystallized sorbic acid is removed, and part of the solvent is reheated to the overhead temperature and fed as reflux through the top of the column into the rectification column. The remaining solvent is, as was originally also the case, used to dilute the sorbic acid polymer being employed. The difference from the prior art in which the reflux necessary for the rectification consists of distillate is that the solvent is used as reflux in the process of the invention.

To achieve the purpose of the invention, it is advantageous for the solvent used as reflux to have been freed as completely as possible from the sorbic acid present in the distillate, but this is not absolutely necessary. However, as the sorbic acid content in the reflux increases there is a decrease in the advantages to be achieved with the process of the invention compared with the prior art. The invention does, however, include these less optimal embodiments.

The flow diagram 1 shows diagrammatically the distillation process used in the prior art for the polyester cleavage, in which distillate taken off at the top of the column (mixture of sorbic acid and solvent) is fed as reflux into the rectification column.

Flow diagram 2 shows diagrammatically the distillation process according to the present invention, in which the solvent which has distilled out is, after removal of the sorbic acid, fed as reflux into the rectification column.

Apart from the effect of increasing the yield, the procedure of the invention also permits an up to 30% increase in capacity, although with at least partial loss of the gain in yield. To achieve the increase in capacity in the procedure of the invention described above with solvent as reflux, part of the solvent in the input is replaced by sorbic acid polyester, i.e. less solvent is used measured by the polyester input in the distillation vessel. Only when the increase in capacity is more than 30% does the yield of sorbic acid fall again to below the yield which can be achieved with the normal procedure corresponding to the prior art.

The arrangement and procedure of the invention for the preparation of sorbic acid thus allows great flexibility in relation to the quantity produced and the plant utilization, with which very rapid responses to market requirements are possible.

The process of the invention for preparing sorbic acid can in principle be carried out as described in DE-AS 1 282 645 without, however, being restricted thereto. To this extent, express reference is made to this publication, and the description of the preparation of sorbic acid using catalytic quantities of an amine (preferably 0.5 to 10% by weight based on the polyester employed) is included in the description of the present invention (cf. concerning this the disclosure from column 3, line 31 onward, with the exception of the sections describing the use of a large excess of amine, the amine simultaneously being catalyst and entrainer for the sorbic acid (distillation)). This reference also applies to the preferred solvents, amines, ratios by weight and/or ratios of amounts of the starting materials and reaction and distillation temperatures described therein.

In particular, reference is made hereinafter to additional particularly advantageous embodiments of the process of the invention.

DE-AS 1 282 645 discloses that secondary or tertiary aliphatic, alicyclic, 5- or 6-membered heterocyclic nitrogen- and/or oxygen-containing or aliphatic-aromatic-substituted amines boiling above 100° C. under atmospheric pressure are suitable as catalysts.

Examples which can be employed very successfully are: methyloctadecylamine, dimethyloctadecylamine, dimethylhexadecylamine, dimethyltetradecylamine, dimethyldodecylamine, dibutyldodecylamine, N,N,N',N'-tetramethylhexamethylenediamine, N,N,N'-trimethyl-N'-phenyl-ethylenediamine, N-octadecylpyrrolidone, N-octadecylpiperidine, N-dodecylmorpholine, N,N'-dipropylpiperazine, α-hexylpyrrolidone, triethylenetetramine, ethylbis(β-ethylaminoethyl)amine, 1-octyldiethylenetriamine, ethylene glycol bis(2-methylaminoethyl ether), dioctadecylamine, diethylenetriamine, trioctadecylamine, trioctylamine, tricyclohexylamine, dimethylstearylamine.

Solvents suitable for obtaining sorbic acid are aliphatic, alicyclic, aromatic hydrocarbons, their chloro, bromo and nitro derivatives, as well as ethers and silicone oils whose boiling point is preferably above 150° C., with preference above 180° C., under atmospheric pressure. However, ketones, esters, carboxylic acids and alcohols with the appropriate boiling range can also be used as solvents although the results are generally not quite as good, because they presumably react to some extent with the reaction mixture. It is expedient to use solvents which are liquid at normal temperatures, boil below 300° C., preferably below 270° C., under atmospheric pressure, and form azeotropic mixtures with the sorbic acid so that they also act simultaneously as carrier or entrainer. Examples are petroleum fractions, dodecane, tetradecane, 5-methyldodecane, dodecene, dicyclohexylmethane, p-di-tertiary-butylbenzene, 1-methylnaphthalene, 2-methylnaphthalene, 1-ethylnaphthalene, tetrahydronaphthalene, diphenyl, naphthalene; halogenated aliphatic, cycloaliphatic or aromatic hydrocarbons such as dichlorododecane, 1,5-dibromopentane, benzotrichloride, o- and m-dibromobenzene, nitro compounds such as nitrobenzene, 2-nitrotoluene, nitriles such as benzyl cyanide, carbonyl compounds such as acetophenone or the heterocyclic 2-acetylthiophene, heterocyclic compounds such as chroman, thiophene, ethers such as resorcinol dimethyl ether, diphenyl ether, safrole, isosafrole, acids such as enanthic acid, α-ethylcaproic acid, caprylic acid, pelargonic acid, Versatic acid, capric acid, esters such as ethyl benzoate, methyl phenylacetate and methyl salicylate. Suitable solvents or diluents are also described in DE-AS 1 059 899, which is expressly incorporated by reference. It is also possible in principle to use mixtures of solvents.

The following examples serve to illustrate the invention.

The starting material used is a polyester-containing reaction product obtained in analogy to example 1 of DE-AS 1 042 573. This entails passing 420 g of ketene into a stirred mixture of 800 g of crotonaldehyde, 1200 ml of toluene and 14.2 g of zinc isovalerate at a temperature between 25 and 35° C. The excess crotonaldehyde and the toluene are removed in vacuo. 1150 g of polyester (sorbic acid polyester) are obtained as residue in the form of a highly viscous, brown-colored liquid. Besides the zinc content of 3000 ppm, this reaction product also contains fractions which cannot be converted into hexadienoic acids (sorbic acid), such as diketene polymers and crotonaldehyde resins.

The fraction which can be converted into hexadienoic acids is determined by basic hydrolysis of a solution of 60 g of sorbic acid polyester in 120 g of toluene with 33 g of potassium hydroxide in 260 g of water at room temperature. This results in potassium sorbate and the potassium salt of 3-hydroxy-4-hexenoic acid in the aqueous phase, from which hexadienoic acids can be obtained by acidification. The polyester fraction which can be converted into hexadienoic acids can be determined by quantitative determination of the two reaction products by HPLC.

The polyester content can be determined with these mild conditions more accurately than described in DE-AS 1 282 645. Thus, the fraction of the crude polyester which can be converted into hexadienoic acids is 89 to 90% and not, as assumed in DE-AS 1 282 645, only 80%. The yields achieved in DE-AS 1 282 645 must therefore be corrected correspondingly, see example 1 (comparative example).

EXAMPLE 1 (COMPARATIVE EXAMPLE)

The apparatus consists of a 1 l 3-neck round-bottom flask (reaction flask) with fitted distillation column. The distillation column has an internal diameter of 40 mm and is packed to a height of 600 mm with glass Raschig rings of diameter 6 mm. The distillation column has a reflux dividing head cooled to 70° C. The condensed distillate is partly returned to the column by the reflux divider and partly collected in a graduated receiver (500 ml) and a 6 l round-bottom flask. The entire apparatus is operated under vacuum; the vacuum is generated by an oil pump with upstream dry-ice cold trap.

260 g of distillation residue from a previous experiment which contains 40% dimethylstearylamine (DMSA) are employed in each case. The apparatus is evacuated to about 30 mbar, and the reaction flask is heated with the oil bath (bath temperature about 220° C.). When the temperature in the reaction flask reaches 180° C., metering (417 g/h) of the initial mixture into the reaction flask is started. As soon as distillate appears, a reflux of 417 g/h is adjusted.

The initial mixture in the reaction flask consists of 350 g of polyester, 2128 g of 2-ethylhexanoic acid, 48 g of DMSA and 14 g of Arcopal® (total quantity 2540 g). After metering of the initial mixture, as yet unreacted polyester is subsequently cleaved by running pure solvent (nonylphenol polyglycol ether) without polyester and without reflux through the apparatus (834 g) for 2 h, followed by distillation for 5 min. The distillate present in the receiver is homogenized by heating to 50 to 55° C. and then cooled with stirring (500 rpm) to 20° C. over the course of 3 h. After this temperature is reached, it is kept at 20° C. for 15 min and then the crude sorbic acid is filtered off with suction and the pure content is determined by gas chromatography. The mother liquor is reused in the next experiment. An 82.1% yield of sorbic acid is obtained. The yield calculated on the basis of the pure polyester, i.e. taking account only of the 90% fraction which can be cleaved to hexadienoic acids, is 91.2%.

EXAMPLE 2

The apparatus consists of a 1 l 3-neck round-bottom flask (reaction flask) with fitted distillation column. The distillation column has an internal diameter of 40 mm and is packed to a height of 600 mm with glass Raschig rings of diameter 6 mm. The distillation column has at its top an inlet heated to 100° C., and an insulated Claisen head with downsloping condenser at 70° C. A graduated, heatable receiver (500 ml) and a 6 l round-bottom flask are connected successively to the condenser. The entire apparatus is operated under vacuum; the vacuum is generated by an oil pump with upstream dry-ice cold trap. 260 g of distillation residue from a previous experiment which contains 40% dimethylstearylamine are used in each case. The apparatus is evacuated to about 30 mbar, and the reaction flask is heated with the oil bath (bath temperature about 220° C.). When the temperature in the reaction flask reaches 180° C., metering (417 g/h) of the initial mixture into the reaction flask is started. As soon as distillate appears, 2-ethylhexanoic acid (likewise 417 g/h, in the first experiment solvent from operation) is metered in at the top of the column through a heat exchanger and the heatable inlet (both heated to 100° C.).

The initial mixture in the reaction flask consists of 350 g of polyester, 2128 g of 2-ethylhexanoic acid, 48 g of DMSA and 14 g of Arcopal® (total quantity 2540 g). At the same time, an equal quantity (2540 g) of 2-ethylhexanoic acid is metered as reflux.

The reaction products and the solvent are distilled out with minimal uncontrolled reflux. After the metering of the initial mixture and of the solvent reflux, pure solvent (2-ethylhexanoic acid) without polyester and without reflux are run through the apparatus (834 g) for 2 h, followed by distillation for 5 min. The distillate present in the receiver is homogenized by heating to 50 to 55° C. and then cooled with stirring (500 rpm) to 20° C. over the course of 3 h. After this temperature is reached, it is kept at 20° C. for 15 min and then the crude sorbic acid is filtered off with suction and the pure content is determined by gas chromatography. The mother liquor is reused in the next experiment to make up the initial mixture and the reflux. An 84.2% yield of sorbic acid is obtained. The yield calculated on the basis of the pure polyester, i.e. taking account only of the 90% fraction which can be cleaved to hexadienoic acids, is 93.6%.

EXAMPLE 3

The setup and procedure corresponds to that in example 2. The quantity of sorbic acid polyester in the initial mixture is increased to 400 g, and the quantity of solvent is reduced to 2078 g. The quantity of dimethylstearylamine and Arcopal and thus the total liquid input per unit time remain the same. A sorbic acid yield of 83.7% is obtained. The yield calculated on the basis of the pure polyester, i.e. taking account only of the 90% fraction which can be cleaved to hexadienoic acids, is 93%.

EXAMPLE 4

The setup and procedure corresponds to that in example 2. The quantity of sorbic acid polyester in the initial mixture is increased to 450 g, and the quantity of solvent is reduced to 2028 g. The quantity of dimethylstearylamine and Arcopal and thus the total liquid input per unit time remain the same. A sorbic acid yield of 82.9% is obtained. The yield calculated on the basis of the pure polyester, i.e. taking account only of the 90% fraction which can be cleaved to hexadienoic acids, is 92.1%.

EXAMPLE 5

The setup and procedure corresponds to that in example 2. The quantity of sorbic acid polyester in the initial mixture is increased to 500 g, and the quantity of solvent is reduced to 1978 g. The quantity of dimethylstearylamine and Arcopal and thus the total liquid input per unit time remain the same. A sorbic acid yield of 80.6% is obtained. The yield calculated on the basis of the pure polyester, i.e. taking account only of the 90% fraction which can be cleaved to hexadienoic acids, is 89.6%.

What is claimed is:

1. A process for the preparation of sorbic acid by thermal cleavage of a polyester prepared from crotonaldehyde and ketene, in the presence of a solvent and of an amine as catalyst with simultaneous off-distillation of the sorbic acid formed and of the solvent through a rectification column with reflux, wherein the reflux consist essentially of the solvent.

2. The process as claimed in claim 1, wherein the solvent forms an azeotropic mixture with the sorbic acid.

3. The process as claimed in claim 1, wherein the boiling point of the solvent is above about 150° C., and below about 300° C.

4. The process according to claim 1, wherein the solvents are entrainers.

5. The process as claimed in claim 1 or 4, wherein the solvent or entrainer is selected from one or more compounds of the group consisting of aliphatic, alicyclic, aromatic hydrocarbons, their chloro, bromo or nitro derivatives, ethers, silicone oils, ketones, esters, carboxylic acids and alcohols the boiling points of all of these are above about 150° C. under atmospheric pressure.

6. The process as claimed in claim 1, wherein the catalyst is selected from one or more compounds of the group consisting of secondary and tertiary aliphatic, alicyclic, 5- and 6-membered heterocyclic nitrogen- or oxygen- containing or nitrogen and oxygen-containing and aliphatic-aromatic-substituted amines all of which boil above about 100° C. under atmospheric pressure.

7. The process as claimed in claim 1, wherein the thermal cleavage of the polyester is carried out at about 160–220° C.

* * * * *